United States Patent [19]

Kuhlmann

[11] 3,947,494

[45] Mar. 30, 1976

[54] QUALITY OF PHTHALIC ACIDS IMPROVED BY HALOACETIC ACID

[75] Inventor: George E. Kuhlmann, Downers Grove, Ill.

[73] Assignee: Standard Oil Company, Chicago, Ill.

[22] Filed: Dec. 20, 1972

[21] Appl. No.: 316,857

[52] U.S. Cl. ............................................. 260/524 R
[51] Int. Cl.$^2$ ........................................ C07C 51/33
[58] Field of Search ................................ 260/524 R

[56] References Cited

UNITED STATES PATENTS

| | | | |
|---|---|---|---|
| 2,833,816 | 5/1958 | Saffer | 260/524 R |
| 3,162,683 | 12/1964 | Jones et al. | 260/524 R |
| 3,674,845 | 7/1972 | Reni et al. | 260/524 R |

FOREIGN PATENTS OR APPLICATIONS

| | | | |
|---|---|---|---|
| 1,148,863 | 4/1969 | United Kingdom | 260/524 R |
| 4,419,247 | 8/1969 | Japan | 260/524 R |

OTHER PUBLICATIONS

Ohta, Kogyo Kagaelar Zasshi, Vol. 63 No. 5 1960 pp. 768–773.

*Primary Examiner*—Anton H. Sutto
*Attorney, Agent, or Firm*—Fred R. Ahlers; Arthur G. Gilkes; William T. McClain

[57] ABSTRACT

Phthalic acids of improved quality are obtained direct from oxidation of xylenes with molecular oxygen in oxidation zone having small amounts of haloacetic acid present in liquid phase acetic acid solution of one or more heavy metal oxidation catalyst and bromide ion releasing bromine-containing compound. Particularly useful haloacetic acids are those having aqueous dissociation constant $K_A$ greater than $1.0 \times 10^{-3}$. Such quality improvement is manifested by decrease in carboxybenzaldehyde and toluic acid impurity contents and/or metal salt content.

5 Claims, No Drawings

QUALITY OF PHTHALIC ACIDS IMPROVED BY HALOACETIC ACID

BACKGROUND OF INVENTION

The discovery of the unique catalysis afforded by the acetic acid solution of the joint use of one or more heavy metal oxidation catalysts and a source of bromide ion for the liquid phase oxidation at a temperature from 50° to 275°C. of aliphatic-substituted aromatic compounds with molecular oxygen to aromatic polycarboxylic acid products was first disclosed in U.S. Pat. No. 2,833,816 which issued May 6, 1958. The use of said unique catalysis for such oxidation of xylenes under liquid phase conditions at 50° to 275°C. made feasible for the first time by catalytic liquid phase air oxidation large scale commercial production of the benzene dicarboxylic acids: ortho-, iso- and terephthalic acids. Since 1958 many improved modes of conduct of such oxidations using the unique combination of heavy metal and bromide ion have been disclosed as advancements of that art. Some improvements were directed to yield improvement per unit of time and other improvements were directed to improved quality and yield of benzene polycarboxylic acid product. In general the improved modes of conduct for said liquid phase oxidation using the unique catalysis involved selective order of addition of catalyst components; scheduling addition of catalyst components; use of either constant temperature or constant pressure; scheduling different rates of oxygen supply; use of sources of oxygen having oxygen contents below and above the oxygen content of air; regulation of water content of acetic acid in the oxidation zone; sequentially staging of two or series connected oxidation zones operated at different temperatures, pressures, oxygen concentration or water concentration; usage of different combinations of heavy metals and types of bromide iron source, e.g. ionic and combined bromine; and combinations thereof as applied to batchwise, semi-continuous and continuous operations. Such improved modes of operation using the unique catalysis did provide for increase of benzene di- and tricarboxylic acid products from the yields demonstrated by the methods of U.S. Pat. No. 2,833,816. For example the yields of iso- and terephthalic acids from the corresponding xylenes were increased to 90–92 mole percent from 75–80 mole percent demonstrated by said patent and with attendant improved decrease of partially oxidized xylene such as aldehydo-benzoic acid and toluic acid which contaminated said phthalic acid products.

Commercially feasible methods were devised for removal of color bodies and/or oxygen-containing aromatic compounds contaminating benzene di- and tri-carboxylic acid products from such improved modes of conduct of the aforementioned liquid phase oxidation using the unique catalysis. Such purifications were directed either to obtension of light colored or white products intended for use in unsaturated polyesters or to obtension of highly pure terephthalic acid product at least 99.9 weight percent purity for direct reaction with a diol in the manufacture of high molecular weight polyesters required for film and fiber manufacture. However, little attention was given since 1958 to the introduction of a new component into the unique catalytic liquid phase oxidation to decrease the appearance of contaminants which are partial oxidation products attendant the oxidation of xylenes to phthalic acid di- and trimethylbenzenes products recovered from said oxidations.

It has been known since 1958 that oxidation of m- or p-xylenes in the presence of the unique catalysis at temperatures in the range of 50° to 120°C. using oxygen gas as oxidant produced iso- or terephthalic acid products containing relatively large amounts, 3 to 10 weight percent, of 3 or 4-formylbenzoic acid and like amounts of m- or p-toluic acids. Oxidations conducted under liquid phase conditions in the presence of the unique catalysis at temperatures above 120°C., i.e. in the range of 120° to 275°C., using oxygen gas or air as source of molecular oxygen did decrease the concentration of formylbenzoic and toluic acid contaminants in iso- and terephthalic acid products from the corresponding xylenes to below 3 weight percent, e.g. 0.5–2.0 weight percent. The improved modes of conduct of the catalytic liquid phase oxidation did little to improve the low temperature (i.e. 50°–100°C.) oxidations.

In addition to aldehydic acid and toluic acid contamination of phthalic acids there is also the problem of contamination by catalyst metals and corrosion metals, a problem unique to preparation of halophthalic acids. Such metals are precipitated by the halophthalic acid during oxidation and cause early termination of the oxidation of haloxylenes.

To make more effective, on a pounds per hour throughput basis, the various commercially available purification routes for phthalic acids it is highly desirable to obtain such acids direct from oxidation in a higher quality by some means in addition to such improved modes of conduct of liquid phase oxidation using the unique catalysis.

SUMMARY OF INVENTION

Phthalic acids and their halogen-containing analogs are obtained in higher quality by the oxidation of xylene hydrocarbons and halogenated analogs thereof with molecular oxygen at a temperature in the range of 50° to 275°C. in an oxidation zone containing a catalytic amount of a haloacetic acid in addition to the liquid phase acetic acid solution of heavy metal oxidation catalyst and bromide ion providing the unique catalysis. The haloacetic acid so used decreases by 50–85% the amount of formylbenzoic (carboxylbenzaldehyde) and toluic acid contamination of the desired phthalic acid product and act as activators of the unique catalysis. The bromoacetic acids not only cause said decrease in aldehydo-acid formation as partial oxidation product but also can be effectively used as the source of bromine component of the unique catalysis. The haloacetic acids are used in catalytic amounts which vary with the xylene to be oxidized as well as the haloacetic acid used. In general, for oxidation of xylene hydrocarbons such catalytic amount is within the range of 0.1 to 12.0 weight percent based on the xylene hydrocarbon to be oxidized. Such use of tri-haloacetic acids also decreases precipitation of catalyst metals by halogenated phthalic acids during oxidation of haloxylenes and prevent early termination of the oxidation. For such use with haloxylenes the catalytic amount of trihaloacetic acids, especially trifluoroacetic acid, is in the general range of 0.5 to 6.0 weight parts per weight part of halogenated xylene.

SPECIFIC EMBODIMENTS

The haloacetic acids useful according to this invention are the mono-, chloro-, bromo- or fluoro- to trichloro-, bromo- and fluoroacetic acids having the aqueous dissociation constant $K_A$ greater than $1 \times 10^{-3}$. Typically illustrative haloacetic acids and their constant $K_A$ are:

| HALOACETIC ACID | |
|---|---|
| Monobromoacetic acid | $1.3 \times 10^{-3}$ |
| Monochloroacetic acid | $1.4 \times 10^{-3}$ |
| Monofluoroacetic acid | $2.6 \times 10^{-3}$ |
| Dichloroacetic acid | $5 \times 10^{-2}$ |
| Trichloroacetic acid | $12 \times 10^{-1}$ |
| Trifluoroacetic acid | $5.9 \times 10^{-1}$ |

Such haloacetic acids are useful, as mentioned above, in small amounts, from 0.1 to 12 weight parts based on the xylene, hydrocarbons but can be as high as 0.5 to 6.0 weight parts of trihaloacetic acids based on monochloro or mono- bromo- to tetrachloro or tetrabromo xylenes to be oxidized and are preferably added with the xylenes or bromo analog thereof but can be added with the acetic acid solution of catalyst components.

The amount of acetic acid used in the catalytic liquid phase oxidation can vary from 2 to 20 weight parts per weight part of the di- or trimethylbenzene or brominated analogs thereof. For low temperature oxidation, 50° to 120°C. and atmospheric to 50 p.s.i.g. pressure the unique catalysis is provided by acetic acid solutions containing cobalt or cobalt and manganese at 13 to 112 weight percent of total metals and 16–116 weight percent of bromide ion based on aromatic compound to be oxidized. For the higher temperature oxidations, 120° to 275°C., there can be used cobalt, manganese mixtures of cobalt and manganese or cobalt, manganese and cerium in total metal concentrations of 0.01 to 1.0 weight percent and bromide ion concentrations of 0.01 to 1.0 weight percent based on the aromatic compound to be oxidized. Bromide ion can be provided by elemental bromine, ionic bromides (e.g. hydrogen bromide, sodium bromide or ammonium bromide) or by co-valent bromine-containing compounds (e.g., potassium bromate, tetrabromoethane, benzylbromide, bromobenzene or bromoacetic acid) which release bromide ion not ionization but rather by thermal release at the temperature at which the oxidation is conducted. Mixtures of ionic and co-valent bromine compounds can be advantageously used as source of bromide ion for the higher temperature oxidations where, in general, heavy metals having an atomic weight between about 50 and about 200 other than cobalt, manganese and cerium or in addition thereto are also useful.

The minimum pressure used in the oxidation zone is that pressure which will provide acetic acid in the liquid phase at temperatures of 50° to 275°C. The source of molecular oxygen oxidant can be any gas-containing molecular oxygen in concentrations from 10 to 100 volume percent. For the low temperature (50°–120°C.) oxidation the source of molecular oxygen can be oxygen gas or mixtures thereof with air or inert gas (e.g. nitrogen or $CO_2$) containing at least 50 volume percent oxygen. But for the higher temperature oxidation (120°–275°C.) the source of molecular oxygen can contain not more than 50 volume percent oxygen as in air or mixtures of oxygen gas with air or inert gas to provide controllable oxidation, which is exothermic, at such higher temperatures.

The catalytic liquid phase oxidations for which this invention provides the aforementioned beneficial improvements have their most practicable application under the following temperature conditions. The low temperature (50°–120°C.) oxidation using high cobalt, or cobalt and manganese to xylene and high acetic acid to xylene ratios provide most feasible production of phthalic acids especially terephthalic acid from p-xylene, per unit of time when conducted using oxygen gas, temperatures of 110° to 120°C. and pressures of 40 to 60 p.s.i.g. even though liquid phase conditions can be maintained in the oxidation zone at pressures of 0 (atmospheric pressure) to 5 p.s.i.g. Such 110° to 120°C. oxidations of p-xylene as in the absence of haloacetic acid provide recovered terephthalic acid product (e.g. by filtration) from fluid oxidation effluent in 80–92 mole percent yields in 80–120 minutes residence periods but contaminated with 5.4 to 1.3 weight percent p-formylbenzoic acid and 0.6 to 0.4 weight percent p-toluic acid. The higher temperature (120°–275° C.) oxidation using both lower acetic acid and lower heavy metal (Co, Mn and/or Ce) ratios to di- or trimethylbenzene provide most feasible production of benzene di- and tricarboxylic acids, especially terephthalic acid from p-xylene, per unit of time when conducted at temperatures in the range of 175° to 250°C. and oxidation zone pressures of 150 to 400 p.s.i.g. For example such oxidation of p-xylene at 200°–210°C. and pressure of 180–210 p.s.i.g. in the absence of haloacetic acid provide recovered terephthalic acid product from fluid oxidation effluent in 90–92 mole percent yields contaminated with but 0.5 to 0.8 weight percent p-formylbenzoic acid and 0.2 to 0.4 weight percent p-toluic acid (both of which are precursors of terephthalic acid) in 40 to 60 minute residence periods.

However, by the use of haloacetic acid having $K_A$ from $1 \times 10^{-3}$ to 0.59 in the above oxidations of p-xylene according to this invention, the amount of contaminant p-formylbenzoic and p-toluic acids in terephthalic acid recovered direct from fluid oxidation effluent are each decreased by from 50 to 85% and at the same time terephthalic acid yield is increased by an amount equivalent to the decrease of the two contaminant precursors of terephthalic acid.

The following illustrative examples are provided to enable one skilled in this art to understand and practice the present invention.

The first illustrative examples demonstrate the beneficial improvements afforded by the use of haloacetic acids in the oxidation of p-xylene with air to terephthalic acid. These p-xylene oxidations are made with air at the oxidating zone temperatures and pressures and haloacetic acid use later indicated. The reactants and catalyst are:

| | |
|---|---|
| 100% Acetic Acid | 1313 Grams |
| Water | 100 Grams |
| p-Xylene | 348 Grams |
| Total Co and Mn Metals | 0.45 Weight Percent on p-Xylene |
| Bromine | 0.22 Weight Percent on p-Xylene |

The oxidation reactions are conducted in an oxidation vessel having a valved air inlet at the bottom; a valved dip-leg p-xylene inlet; a heating mantle, a water cooled reflux condenser with a pressure regulating valve in its gas discharge line; a gas-vapor transfer line connecting the vapor space of said otherwise sealed vessel with said condenser; and a gas sampling top line which has a dry ice (solid $CO_2$) cooled trap and an oxygen analyzer in said gas discharge line beyond the pressure reducing valve and condenser. To such oxidation vessel there is charged the acetic acid having dissolved therein the water and sources of cobalt, manganese and bromine. The pressure regulating valve is set at operating pressure and the oxidation vessel is pressured to said pressure with nitrogen gas. The acetic acid solution is heated to oxidation temperature which causes substantially all the nitrogen gas to be discharged from the system. Thereafter the 348 grams of p-xylene is pumped and air injected simultaneously into the hot acetic acid solution at correlated rates to provide, on acetic acid free basis, a small amount of oxygen in the condenser discharge gas. After all the xylene has been pumped in, air injection alone is continued for about 10 to 20 minutes until the oxygen content of the condenser discharge gas is 20 percent by volume. The reaction vessel contents are discharged with aid of nitrogen gas pressure, cooled to about 50°C. and charged to a filter to recover terephthalic acid product. The reaction vessel is rinsed to remove all product and the rinsed solids are added to the filter cake product.

The total terephthalic acid product so recovered is washed with warm acetic acid and dried. The dried product is analyzed for p-formylbenzoic acid and p-toluic acid contents and its acid number determined. The foregoing oxidation is a semi-continuous process, one of the improved methods of conduct of the aforementioned unique catalytic liquid phase oxidation methods. The conditions and results of four such oxidations using trifluoroacetic acid (TFA) as the haloacetic acid and one such oxidation using no haloacetic acid as a control basis are listed in TABLE I.

TABLE I

| | TRIFLUOROACETIC ACID EFFECT ON p-XYLENE OXIDATION | | | | |
|---|---|---|---|---|---|
| Example No. | Control | 1 | 2 | 3 | 4 |
| Pressure, p.s.i.g. | 250 | 300 | 295 | 265 | 300 |
| Initial Temperature, °F. | 410 | 406 | 379 | 418 | 412 |
| Maximum Temperature, °F. | 427 | 432 | 430 | 447 | 497 |
| Average Temperature, °F. | 410 | 420 | 425 | 415 | 435 |
| Run Time, Minutes | 87 | 84 | 88 | 105 | 18 (1) |
| Pump Time, Minutes | 66 | 69 | 67 | 65 | 17 |
| TFA, Weight % (2) | 0 | 1.91 | 2.89 | 5.3 | 6.2 |
| Product | | | | | |
| Dry Product Weight Percent | 126 | 132 | 117 | 129 | 0 |
| Acid No. (675 Theory) | 660 | 632 | 676 | 669 | — |
| Percent 4-CBA | 1.37 | 0.59 | 0.22 | 1.58 | — |
| Percent p-Toluic Acid | 0.44 | 0.11 | 0.041 | 0.46 | — |

(1) Run stopped because oxidation inhibited.
(2) Based on p-xylene.

The above data demonstrates that trifluoroacetic acid used in amounts above about 3.0 weight percent of p-xylene is not effective for diminishing the content of 4-carboxylbenzaldehyde (4-CBA) and p-toluic acid in the terephthalic acid product but its use at lower amounts based on p-xylene does provide a substantial advantage for p-xylene oxidation to higher quality terephthalic acid.

Likewise, trifluoroacetic acid beneficially effects o-xylene oxidation over a range somewhat broader relative to p-xylene. This can be demonstrated by the oxidation of 360 grams o-xylene in the same manner as described for p-xylene oxidation. The oxidation conditions and results are shown in the following TABLE II. In this table the results are shown in grams of o-phthalic acid and its related co-products calculated from analysis of total solids remaining after evaporation of acetic acid, trifluoroacetic acid and water from the oxidation effluent. Such showing provides a more valid representation of results because o-phthalic acid and its related co-products, unlike terephthalic acid and its related co-products, are much more soluble in acetic acid solvent making unrepresentative reporting only filter cake yield and impurity contents.

TABLE II

| | TRIFLUOROACETIC ACID EFFECT ON o-XYLENE OXIDATION | | | | | | |
|---|---|---|---|---|---|---|---|
| Example No. | Control | 5 | 6 | 7 | 8 | 9 | 10 |
| Pressure, p.s.i.g. | 300 | 300 | 300 | 295 | 320 | 320 | 320 |
| Temperature °F., Initial | 380 | 380 | 380 | 401 | 380 | 376 | 376 |
| Temperature °F., Maximum | 418 | 426 | 424 | 428 | 426 | 424 | 436 |
| Temperature °F., Average | 410 | 415 | 415 | 415 | 415 | 415 | 415 |
| Run Time, Minutes | 89 | 91 | 86 | 83 | 84 | 83 | 86 |
| Pump Time, Minutes | 62 | 62 | 62 | 62 | 62 | 62 | 62 |
| TFA, Percent* | 0 | 1.28 | 1.89 | 2.78 | 3.20 | 4.88 | 5.97 |
| Products: | | | | | | | |
| o-Toluic Acid, Grams | 35.7 | 19.3 | 23.8 | 26.0 | 34.0 | 44.8 | 49.0 |
| o-Phthalic Acid, Grams | 322 | 382 | 364 | 369 | 353 | 329 | 324 |
| Phthalide, Grams | 25.7 | 20.2 | 16.6 | 13.8 | 19.7 | 21.2 | 20.2 |
| 2-CBA, Grams | 17.8 | 13.3 | 13.3 | 10.95 | 13.4 | 16.8 | 13.8 |

*Based on o-xylene charge.

From the above data o-phthalic acid increase over the control held up over the range of about 1.3 to about 6.0% trifluoroacetic acid and phthalide and 2-carboxybenzaldehyde (2-CBA) co-products diminished over that range. But effective diminishing of o-toluic acid co-product appears to cease between about 2.8 and 3.2% (i.e. 3.0%) trifluoroacetic acid.

Examples 11–16

The preparation of halophthalic acids in the presence of trifluoroacetic acid (TFA) prevents, to a useful extent, catalyst metal precipitation by the halophthalic acid as it forms making catalyst metal unavailable for its essential function. This can be illustrated by the following oxidations of tetrabromo-m-xylene, tetrabromo and tetrachloro-p-xylene. For example, two such oxidations conducted batchwise at 385°–440°F.

Examples 12–23

The 250 p.s.i.g. oxidations of p-xylene are again conducted using the semi-continuous mode of operation described for Examples 1–4 except in place of TFA there are used monochloro-, monobromo- and monofluoro-acetic acids. The effect on product quality by use of said monohaloacetic acids at their designated concentrations in acetic acid solvent are shown in TABLE IV.

TABLE IV

MONOHALOACETIC ACID EFFECT ON p-XYLENE OXIDATION

| Example No. | Control | 17 | 18 | 19 | 20 | 21 | 22 | 23 |
|---|---|---|---|---|---|---|---|---|
| Temperature °F. | | | | | | | | |
| Initial | 410 | 380 | 394 | 380 | 380 | 380 | 380 | 388 |
| Maximum | 427 | 431 | 418 | 416 | 424 | 425 | 424 | 425 |
| Average | 410 | 420 | 410 | 410 | 415 | 415 | 415 | 415 |
| Run Time, Mins. | 87 | 95 | 78 | 84 | 83 | 89 | 82 | 85 |
| Pump Time, Mins. | 66 | 66 | 66 | 66 | 66 | 66 | 66 | 66 |
| Monohaloacetic Acid %* | 0 | 3.59 | 1.15 | 3.45 | 3.62 | 5.17 | 7.2 | 11.7 |
| Halogen | — | Cl | Br | Br | F | F | F | F |
| Dry Product %* | 126 | 139 | 126 | 144 | 141 | 148 | 147 | 146 |
| Terephthalic Acid, Wt. % | 95.86 | 99.67 | 99.0 | 96.3 | 96.59 | 95.6 | 97.84 | 98.19 |
| p-Toluic Acid, Wt. % | 0.30 | 0.26 | 0.23 | 0.17 | 0.26 | 0.24 | 0.12 | 0.18 |
| 4-CBA, Wt. % | 1.37 | 1.16 | 0.98 | 0.79 | 1.00 | 1.10 | 0.57 | 0.79 |
| Acid No. (Theory 675) | 660 | 670 | 667 | 672 | 669 | 672 | 673 | 675 |

*Based on p-xylene charge.

and 250 p.s.i.g. each with 200 grams of tetrabromo or tetrachloro-p-xylene in 1250 grams acetic acid containing of 0.4 total weight percent of Co and Mn (calculated as metals) and 0.2 weight percent bromine terminate at about 12–14 weight percent yield of the respective tetrabromo- and tetrachloro-phthalic acids. But when the oxidations of tetrabromo- and tetrachloro-p-xylene and tetrabromo-m-xylene are conducted at the same temperature but under the other conditions in TABLE III in the presence of TFA, the desired carboxylic acid products are obtained in substantially higher yields, as shown even though concentrations of catalytic components are lower.

Examples 24–28

In Examples 18 and 19 the amounts of monobromoacetic acid (1.15 and 3.44% of p-xylene charged) provided bromine source in addition to that of the catalyst components. As part of the investigative oxidations shown in TABLE IV other oxidations (Examples 24–28) conducted using different amounts of monobromoacetic acid on p-xylene charged for its impurity reducing effect and in addition to provide the sole source of bromine are shown in TABLE V. These oxidations were also conducted with 348 grams p-xylene, and the same metals and total metals concentration

TABLE III

EFFECT OF TRIFLUOROACETIC ACID ON HALOXYLENE OXIDATION

| Haloxylene | Grams | Catalyst Components Weight Percent On The Xylene | | Solvent-Grams | | Pressure p.s.i.g. | Product Weight Percent |
|---|---|---|---|---|---|---|---|
| | | Metals | Bromine | Acetic Acid | TFA | | |
| Br$_4$-m-xylene | 200 | 2.5 | 3.75 | 1250 | 0 | 250 | 12 |
| Br$_4$-m-xylene | 200 | 1.86 | 2.79 | 480 | 760 | 300 | 45 |
| Br$_4$-m-xylene | 200 | 1.64 | 3.28 | 700 | 1050 | 350 | 50 |
| Br$_4$-p-xylene | 200 | 1.86 | 2.79 | 480 | 760 | 350–400 | 70 |
| Cl$_4$-p-xylene | 200 | 1.86 | 2.79 | 480 | 760 | 300 | 55 |
| Cl$_4$-p-xylene | 200 | 1.06 | 1.59 | 880 | 180 | 300 | 71 |

While the foregoing oxidation conditions are not optimum for oxidation of the tetrahaloxylenes to the corresponding tetrahalophthalic acids, the improvement trends shown above, not magnitude, are typical for product yield enhancement.

based on p-xylene, the same amount (1313 grams) acetic acid and the same 250 p.s.i.g. pressure as used for Examples 1–5 and 17–23. Examples 18 and 19 are again shown in TABLE V for convenience of reference for the entire monobromoacetic acid use series of oxidations.

TABLE V

MONOBROMOACETIC ACID EFFECT ON p-XYLENE OXIDATION

| Example No. | 18 | 19 | 24 | 25 | 26 | 27 | 28 |
|---|---|---|---|---|---|---|---|
| Temperature °F. | | | | | | | |
| Initial | 394 | 380 | 380 | 380 | 380 | 380 | 380 |
| Maximum | 418 | 416 | 426 | 421 | 421 | 425 | 418 |
| Average | 410 | 410 | 415 | 415 | 415 | 415 | 405 |
| Run Time, Mins. | 78 | 84 | 83 | 82 | 79 | 79 | 76 |

TABLE V-continued

MONOBROMOACETIC ACID EFFECT ON p-XYLENE OXIDATION

| Example No. | 18 | 19 | 24 | 25 | 26 | 27 | 28 |
|---|---|---|---|---|---|---|---|
| Pump Time, Mins. | 66 | 66 | 66 | 66 | 66 | 66 | 66 |
| Monobromoacetic Acid, %* | 1.15 | 3.45 | 0.77 | 3.45 | 5.17 | 2.01 | 3.24 |
| Total Bromine %* | 1.275 | 2.594 | 0.442 | 1.98 | 2.97 | 1.16 | 1.86 |
| Dry Product, %* | 126 | 144 | 133 | 156 | 137 | 146 | 154 |
| Terephthalic Acid, Wt. % | 99.0 | 96.3 | 95.74 | 94.7 | 98.98 | 97.61 | 98.12 |
| p-Toluic Acid, Wt. % | 0.23 | 0.17 | 0.31 | 0.11 | 0.071 | 0.096 | 0.048 |
| 4-CBA, Wt. % | 0.98 | 0.79 | 1.09 | 0.53 | 0.33 | 0.50 | 0.23 |
| Acid No. (Theory 675) | 667 | 672 | 669 | 673 | 674 | 672 | 668 |

*Based on p-xylene charge.

The "Total Bromine %" shown in TABLE V is calculated on the assumption that all bromine in monobromoacetic acid is or becomes available as bromine catalyst component during oxidation and such bromine is added to the bromine from other source for Examples 18 and 19 for comparative purposes because in the remaining examples, as before mentioned, bromine from such other source was omitted. Said assumption that monobromoacetic acid liberates bromine at the oxidation temperatures (380°–426°F.) involved appears to be valid from the results of Example 24 because, in that example, the only bromine supplied is from monobromoacetic acid and because in the absence of any bromine (i.e. catalysis provided by only Co and Mn) an oxidation of p-xylene at a temperature in the range of 380°–426°F. and at a pressure of 250 p.s.i.g. produces mainly p-toluic acid and only 3–20 weight percent terephthalic acid based on p-xylene charged.

In Examples 27 and 28 about 60% and 75%, respectively, of the total monobromoacetic acid was added to the p-xylene pumped into the oxidation vessel containing the acetic acid solution of catalyst metals and the remaining 40 or 25% of the monobromoacetic acid. Such use of monobromoacetic acid is advantageous as can be seen from a comparison of results from Example 28 v Example 19 because of the higher terephthalic acid yield and lower contaminant amounts of p-toluic acid and 4-CBA.

The monohaloacetic acids unlike trifluoroacetic acid (TFA) do not appear to have an oxidation inhibiting effect. TFA used up to about 3% of p-xylene weight reduces p-toluic acid and 4-CBA contaminants in terephthalic acid filter cake, but TFA use over about 3% inhibits p-xylene oxidation. The same range of TFA (i.e. up to about 3 weight percent) diminishes o-toluic acid and 2-CBA contaminants of o-phthalic acid during o-xylene oxidation but does not over the range of 3–6% on o-xylene inhibit its oxidation. Such use of TFA with p-xylene and o-xylene results in about 76% and 39% maximum decrease, respectively, of 4-CBA and 2-CBA. However, TFA is an exceedingly strong, corrosive acid and as a result even causes corrosion of titanium at low concentrations of TFA (0.3 to 0.8%) on acetic acid solvent at oxidation temperatures.

The monohaloacetic acids, while much less corrosive than TFA, are at least as effective, as the foregoing data (TABLES IV and V) demonstrate, catalytic adjuncts for diminishing both carboxybenzaldehyde and toluic acid contaminants. Of the monohaloacetic acid catalysis adjuncts, monobromoacetic acid is as effective as TFA in diminishing p-toluic acid and 4-CBA contaminants of terephthalic acid and reaches its optimum value in the range of 2.0 to 6% of p-xylene when 60 to 75% is charged with the p-xylene. Such use of monobromoacetic acid during oxidation of p-xylene decreases 4-CBA and p-toluic acid contaminants by about 85% of those contaminants appearing in terephthalic acid produced in the absence of haloacetic acids.

The oxidations of m-xylene and o-xylene as well as p-xylene benefit by the use of catalytic amounts of haloacetic acids of aqueous dissociation constant $K_A$ of greater than $1.0 \times 10^{-3}$ and especially benefit by the use of 0.5 to 5 weight percent of monobromoacetic acid based on such xylenes. The beneficial use of monobromoacetic acid during oxidation of such xylenes is two-fold: decrease of carboxybenzaldehyde and toluic acid contaminants and provision of source of bromine.

The invention claimed is:

1. A method for preparing a phthalic acid of improved quality by the oxidation of a xylene hydrocarbon with molecular oxygen in an oxidation zone containing a liquid phase of acetic acid solvent having dissolved therein one or more of cobalt, manganese or cerium and bromine as catalyst components at a temperature in the range of 50° to 275°C., which improvement consists essentially of also having in the acetic acid solution a catalytic amount of a mono-haloacetic acid having an aqueous dissociation constant $K_A$ greater than $1.0 \times 10^{-3}$ wherein said catalytic amount is in the range of 0.1 to 12 weight percent of the xylene.

2. The method of claim 1 wherein the monohaloacetic acid is monobromoacetic acid.

3. The method of claim 2 wherein the catalytic amount of monobromoacetic acid is in the range of about 2.0 to about 6.0 weight percent of p-xylene hydrocarbon.

4. The method of claim 3 wherein monobromoacetic acid is the sole source of bromine for catalysis at a temperature in the range of 380° to 426°F.

5. The method of claim 4 wherein 40 to 25% of the catalytic amount of monobromoacetic acid is charged with the acetic acid solution of catalyst metals in the oxidation zone and 60 to 75% of the monobromoacetic acid is charged with p-xylene.

* * * * *